(12) United States Patent
Zollinger et al.

(10) Patent No.: US 7,878,200 B2
(45) Date of Patent: Feb. 1, 2011

(54) INFANT HEADGEAR FOR SUPPORTING A PATIENT AIRWAY INTERFACE DEVICE

(75) Inventors: Chris Zollinger, Chino Hills, CA (US);
Brian Pierro, Yorba Linda, CA (US);
Kelly Williams, Riverside, CA (US);
Talya Reilly, Chicago, IL (US)

(73) Assignee: CareFusion 2200, Inc., San Diego, CA (US)

( * ) Notice: Subject to any disclaimer, the term of this patent is extended or adjusted under 35 U.S.C. 154(b) by 1080 days.

(21) Appl. No.: 11/354,285

(22) Filed: Feb. 13, 2006

(65) Prior Publication Data

US 2007/0186931 A1   Aug. 16, 2007

(51) Int. Cl.
*A62B 18/08*   (2006.01)

(52) U.S. Cl. .............................. 128/207.11; 128/201.22

(58) Field of Classification Search ............ 128/207.11, 128/201.22, 206.13, 206.21, 206.27; 602/17, 602/74
See application file for complete search history.

(56) References Cited

U.S. PATENT DOCUMENTS

| | | | |
|---|---|---|---|
| 3,063,167 A | 11/1962 | Scholl | |
| 4,078,660 A | 3/1978 | Lerro | |
| 4,117,554 A | 10/1978 | Palumbo | |
| 4,339,151 A | 7/1982 | Riggs | |
| 4,852,186 A | 8/1989 | Landis | |
| 5,465,428 A | 11/1995 | Earl | |
| 5,481,763 A | 1/1996 | Brostrom et al. | |
| 6,805,117 B1 | 10/2004 | Ho et al. | |
| 6,860,268 B2 | 3/2005 | Bohn et al. | |
| 6,889,689 B1 * | 5/2005 | Neuman ................. | 128/201.22 |
| 7,442,177 B1 * | 10/2008 | Garelick et al. ............... | 602/21 |
| 7,451,531 B2 * | 11/2008 | Israel et al. .................... | 24/442 |
| 2004/0112377 A1 * | 6/2004 | Amarasinghe et al. . | 128/201.22 |
| 2005/0061326 A1 * | 3/2005 | Payne, Jr. .............. | 128/206.11 |
| 2005/0268916 A1 * | 12/2005 | Mumford et al. ....... | 128/207.13 |
| 2006/0118119 A1 * | 6/2006 | Berthon-Jones et al. ...................... | 128/207.11 |
| 2006/0283460 A1 * | 12/2006 | Brown et al. ........... | 128/206.24 |

FOREIGN PATENT DOCUMENTS

GB    2 401 531 A    11/2004

OTHER PUBLICATIONS

PCT Search Report mailed Oct. 19, 2007 (10 pgs.).

* cited by examiner

*Primary Examiner*—Justine R Yu
*Assistant Examiner*—Colin Stuart
(74) *Attorney, Agent, or Firm*—Dicke, Billig & Czaja, PLLC

(57) ABSTRACT

A headgear for securing a patient airway interface device to a patient's head, and in particular an infant patient. The headgear includes a central body, first and second forehead straps, and first and second lower straps. The forehead straps extend from opposite side of the central body. The lower straps also extend from opposite sides of the central body, and are inferiorly spaced from a corresponding forehead strap. Upon application to a patient's head, the central body and the forehead straps establish a line of attachment extending from the patient's forehead to a nape of the patient's neck (i.e., adjacent the occipital bone). The lower straps are then available for connecting an airway interface piece to the headgear.

28 Claims, 5 Drawing Sheets

INFANT HEADGEAR FOR SUPPORTING A PATIENT AIRWAY INTERFACE DEVICE

BACKGROUND OF THE INVENTION

The present invention relates to headgear for use with an airway interface device or system. More particularly, it relates to headgear applied to an infant's head for supporting component(s) of an airway interface device or system, such as a patient interface portion of an infant nasal continuous positive airway pressure (nCPAP) system.

A variety of different therapies are delivered to a patient via the patient's nasal airways, such as delivery of breathable gases (e.g., oxygen). As another example, CPAP therapy has been employed for many years to treat patients experiencing respiratory difficulties and/or insufficiencies. In general terms, CPAP therapy entails the continuous transmission of positive pressure into the lungs of a spontaneously breathing patient throughout the respiratory cycle. More recently, CPAP therapy has been advanced as being useful in assisting patients with under-developed lungs (in particular, infants and especially premature infants or neonates) by preventing lung collapse during exhalation and assisting lung expansion during inhalation.

With these and other treatments, it is necessary to attach or secure one or more components to the patient's head. For example, air supply and/or exhaust tube(s) must be connected to the patient's airways and in turn, secured to the patient's head so as to not easily dislodge once connected. Typically, the supply tube(s) terminate in a conventional airway interface apparatus, such as a mask, nasal prongs, endotracheal tube, etc. With this approach, the interface apparatus is itself secured to the patient, such as by an elastic strap extending around a crown of the patient's head. With certain therapies, components in addition to the interface piece (e.g., mask or nasal prongs) must be secured relative to the patient. Certain CPAP formats, and in particular nasal CPAP (or "nCPAP") systems, include not only the patient interface piece (otherwise adapted to interface with the patient's nasal airways) but also a CPAP generator adapted to create or generate a continuous positive airway pressure as well as various tubes extending to and from the CPAP generator. It is preferred that the CPAP generator be positioned in highly close proximity to the patient interface piece. As a result, the CPAP generator must be supported relative to the patient, along with the tube(s) extending to and from the generator. Other respiratory therapy systems have similar requirements.

In light of the above, a variety of different headgears have been developed for mounting and supporting the airway interface component(s) to a patient's head. As a general statement, headgear design efforts have been premised upon the perceived needs of adult patients. Adult patients oftentimes sit or stand upright when receiving the therapy in question, such that a majority of the airway interface component(s) is not located on (i.e., directly supported by) the patient's head. In fact, many adult airway interface headgears are concerned with maximizing mobility of the patient while wearing the device. To this end, it is common for adult headgear to be tightly strapped about the patient's head, and in particular about a crown of the patient's head. While patient comfort is desired, virtually no concern is given to possible trauma caused by pressure points created on the patient's head by the headgear once applied. An adult cranium is not readily damaged by the pressure associated with an even tightly strapped headgear, and the skin of an adult patient's head will typically not be damaged under normal conditions. Unfortunately, for other classes of patients, these factors cannot be dismissed.

Infants (especially premature infants or neonates) are particularly ill-suited for conventional airway interface headgear. Because an infant patient will not be upright, the airway interface device must be supported on or by the infant's head or face. Where the airway interface device entails more than a simple interface piece (e.g., CPAP generator and associated tubing in addition to a mask or nasal prongs), this presents a fairly significant design constraint, particularly in light of the relatively small surface area of an infant's head. In addition, infants are highly susceptible to pain and even long-term trauma when subjected to even a minor level of focused pressure. For example, headgear that generates a small, localized force can cause pressure sores and even necrosis on the infant's skin; under either condition, the infant's inherently low tolerance to pain will result in a strong resistance to wearing the headgear for even short periods. Further, an infant's skull is acutely underdeveloped and quite malleable. As such, headgear-related pressure points can cause positionable head molding.

In recognition of the above, some efforts have been made to design airway interface headgear adapted to better meet the needs of infant patients. The common approach for reducing pressure points on the infant's head is to employ a bonnet-like configuration that otherwise serves as the primary means of attachment. The bonnet fits over the infant patient's head and, in theory, evenly distributes pressure about the head. The bonnet typically forms one or more openings through which straps extending from the airway interface component(s) are threaded. While viable, the bonnet-type approach has several possible deficiencies. A size of the bonnet cannot be adjusted; as such, a hospital or other caregiver facility must maintain a large inventory of differently-sized headgears to accommodate different patients. Along these same lines, it may be difficult to consistently select the best-sized headgear for a particular patient. Further, due to the enclosed nature of the bonnet, application of the bonnet-type headgear to an infant patient often requires more than one caregiver. Similarly, assembly of the airway interface component(s) to the bonnet (e.g., threading the airway interface straps to the bonnet) can be a difficult and time-consuming task. Also, the bonnet, by design, covers nearly an entirety of the infant's head. For many infant patients, therapies in addition to the respiratory therapy in question are required, and are performed through the head (e.g., intravenous therapies delivered through a vein in the patient's head). Under these circumstances, the bonnet presents a distinct impediment and will required caregiver modification.

In light of the above, a substantial need exists for an improved airway interface headgear designed for use with infants. The headgear can be employed with a variety of airway-related therapy systems, for example nCPAP systems.

SUMMARY OF THE INVENTION

Some aspects in accordance with principles of the present invention relate to a headgear for securing a patient interface device to a patient's head, such as an infant patient's head. The headgear is transitionable from a flat state to a wrapped state when applied to the patient's head and includes a central body, first and second forehead straps, and first and second lower straps. The central body defines, in the flat state, a top portion terminating in a top end and a bottom portion terminating in a bottom end. The central body is adapted to be positionable at a rear of the patient's head whereby the bottom portion is adjacent an occipital bone of the patient's head. The first and second forehead straps extend from opposite sides, respectively, of the central body. Each forehead strap includes or defines a trailing segment and a leading segment. The trailing segment extends from the central body, whereas the leading segment extends from the trailing segment. In the flat state, the trailing segment extends in a first spatial direction and the leading segment extends in a second spatial direction, with the second direction being different from the first direction. Finally, the first and second lower straps extend from opposite sides, respectively, of the central body and are laterally spaced from a corresponding one of the forehead straps in a direction opposite the top end of the central body. With this configuration, the headgear can be wrapped about a patient's head, with the central body and the forehead straps establishing a primary line of attachment from immediately below the occipital region (e.g., a nape of the neck) of the patient's head to the patient's forehead. In one embodiment, the headgear is configured to such that in the wrapped state, the top portion conforms to a curvature of a rear of the patient's head, thus minimizing possible pressure points and/or positionable head molding. In other embodiments, the headgear includes a vertical strap extending from the top end of the central body.

Yet other aspects in accordance with principles of the present invention relate to a headgear for securing a patient interface device to a patient's head, such as an infant patient's head. The headgear is transitionable from a flat state to a wrapped state when applied to the patient's head, and includes a central body, first and second forehead straps, and first and second lower straps. The central body defines a top portion terminating in a top end and a bottom portion terminating in a bottom end. The central body is sized and adapted to be positionable at a rear of a patient's head such that in the wrapped state, the bottom portion is adjacent an occipital bone of the patient's head and the top portion does not extend around the patient's head. The forehead straps extend from opposite sides, respectively, of the central body, and are sized and adapted to be positionable across a forehead of the patient's head in the wrapped state. The first and second lower straps extend from opposite sides, respectively, of the central body, and are laterally spaced from a corresponding one of the forehead straps. Further, the lower straps are sized and adapted to be positionable adjacent an upper lip of the patient's head in the wrapped state. With the above in mind, the headgear is sized and adapted such that when applied to a patient's head in the wrapped stated, portion(s) the patient's cranium remains exposed. In one embodiment, the central body is sized and adapted to cover the patient's ears and match the contours of a rear of the patient's head in the wrapped state.

Yet other aspects in accordance with principles of the present invention relate to a combination headgear and patient interface device. The patient interface device includes a nasal piece for directly fluidly interfacing with nares of an infant patient. The headgear includes a central body, first and second forehead straps, and first and second lower straps. The headgear is transitionable from a flat state to a wrapped stated when applied to a patient's head, and is configured to support the nasal piece relative to the patient's head in the wrapped state. With this in mind, the central body defines a top portion terminating in a top end and a bottom portion terminating in a bottom end. The central body is adapted to be positionable at a rear of a patient's head whereby the bottom portion is at a nape of a neck of the patient's head. The forehead straps extend from opposite sides of the central body, respectively, with each forehead strap including a trailing segment extending from the central body in a first direction and a leading segment extending from the trailing segment in a second direction. The first and second lower straps extend from opposite sides of the central body, respectively, and are laterally spaced from a corresponding one of the forehead straps. With this in mind, the patient interface device and the headgear are adapted such that when applied to a patient's head, the forehead straps and the central body secure the headgear to the patient, and the lower straps secure the nasal piece to the headgear. In one embodiment, the patient interface device further includes a support block maintaining a plurality of tubes, and further wherein the headgear is adapted to support the support block relative to the patient's forehead in the wrapped state.

DETAILED DESCRIPTION OF THE INVENTION

Figure 1:
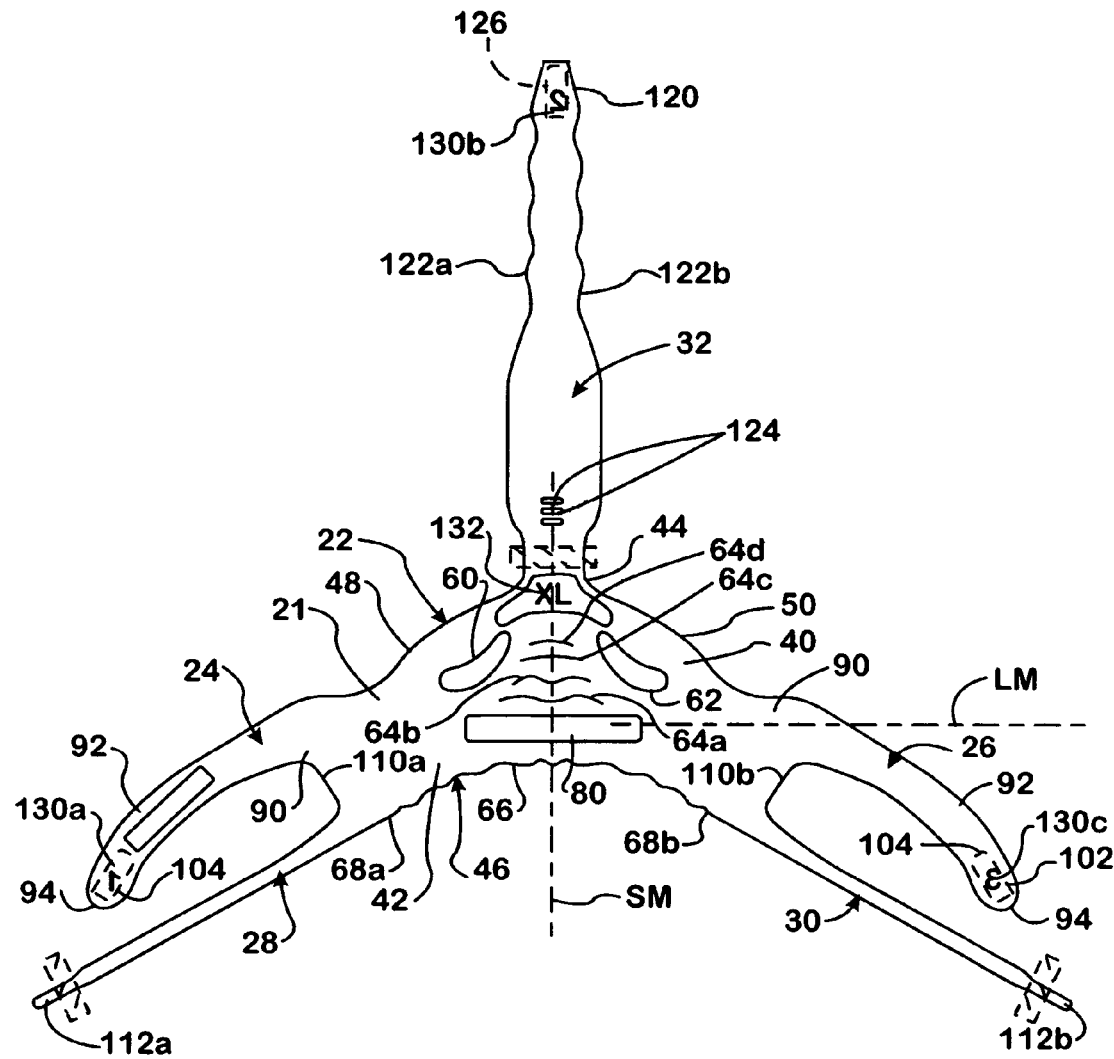
FIG. 1 is a top plan view of a headgear in accordance with principles of the present invention.

One embodiment of a headgear 20 in accordance with principles of the present invention for use with a patient airway interface system is shown in FIG. 1. As a point of reference, the headgear 20 is adapted to be transitionable from a flat or two-dimensional state (as shown in FIG. 1) to a wrapped or three-dimensional state (shown, for example, in FIGS. 2A-2C) when applied to a patient's head, and is, in one embodiment, adapted and sized for use with an infant (e.g., pre-mature infant or neonate). As a point of reference, FIG. 1 illustrates an interior surface 21 (referenced generally) of the headgear 20 (i.e., the side or surface of the headgear 20 intended to contact the patient's head). With this in mind, and relative to the flat state of FIG. 1, the headgear 20 includes a central body 22, first and second forehead straps 24, 26, first and second lower straps 28, 30, and a vertical strap 32. Details on the various components are provided below. In general terms, however, the forehead straps 24, 26 extend from opposite sides, respectively, of the central body 22, as do the lower straps 28, 30. The lower straps 28, 30 are laterally spaced from a corresponding one of the forehead straps 24, 26. The vertical strap 32 extends from a top of the central body 22. When applying the headgear 20 to a patient's head, the central body 22 is placed at a rear of the patient's head. The headgear 20 is transitioned to the wrapped state whereby the forehead straps 24, 26 wrap about the patient's forehead and maintain the vertical strap 32 that is otherwise disposed sagitally across the patient's head. Finally, the lower straps 28, 30 extend toward an upper lip of the patient's head, and serve to secure an airway interface component (not shown) to the headgear 20. In the wrapped state, the central body 22 conforms and supports a rear of the patient's head, yet the headgear 20 as a whole does not encompass an entirety of the cranium.

The central body 22 is, in one embodiment, generally sized in accordance with an expected head circumference of a range of infant patients, and in particular to not extend around a top of an infant patient's head. In other words, the central body 22 is not a bonnet. With this in mind, the central body 22 generally defines a top portion 40 and a bottom portion 42. As a point of reference, directional terminology as used throughout this specification, such as "top," "bottom," "upper," "lower," etc., are with reference to the particular view being discussed and is in no way limiting. The top portion 40 terminates in a top end 44 (referenced generally), whereas the bottom portion 42 terminates in a bottom end 46. First and second opposing sides 48, 50 extend between the top end 44 and the bottom end 46, with the sides 48, 50 being more clearly identifiable along at least a portion of the top portion 40. In recognition of a spatial orientation of the headgear 20 when applied to a patient's head, the central body 22 can be characterized as generally defining a sagittal mid-line SM and coronal mid-line CM.

As will be made more clear below, the central body 22 can assume a variety of sizes most appropriate for a particular range of patients. In more general terms, however, the top portion 40 is sized to wrap about or support the occipital bone and surrounding regions (e.g., skull plates, bones, etc.), whereas the lower portion 42 is sized to engage a nape of the neck (i.e., that portion of the patient's head immediately inferior the occipital bone). In this regard, in one embodiment, the top portion 40 tapers in width from the bottom portion 42 to the top end 44, with a perimeter thereof (i.e., the opposing sides 48, 50 along the top portion 42) defining a curvature. This tapered, curved configuration ensures that a majority of the patient's skull remains exposed upon application of the headgear 20 (i.e., the central body 22 does not encompass or cover a majority of the patient's cranium). However, the top portion 40 provides sufficient surface area to encompass or cover a rear portion of the patient's head. For infant patients, this is of great benefit as the infant's head will be laying on top of the central body 22 during use, such that were the top portion 40 not provided, various pressure point(s) would likely be created against the infant's head; further, the occipital bone of the infant's head would be unsupported and project into possible contact with other surfaces, possibly leading to positionable head molding. The top portion 40 minimizes opportunities for these and other possible problems, effectively creating a three-dimensional cupping about the rear portion of the patient's head. As described below, other features in accordance with some embodiments combine with the curvature of the opposing sides 48, 50 to ensure that when wrapped or cupped about the rear portion of the patient's head, the top portion 40 material does not overtly buckle, but instead conforms to the natural rear head contour.

In one embodiment, the top portion 40 forms first and second openings 60, 62 that facilitate movement of a patient's head in a z-direction (i.e., into and out of the plane of FIG. 1), along with cupping of the top portion about the patient's head in the z-direction as described above. The openings 60, 62 can assume a variety of shapes and sizes, and in one embodiment are teardrop or kidney bean-shaped as shown, and have a convex perimeter shape relative to the sagittal mid-line SM of the headgear 20 (and thus relative to a patient's head upon application of the headgear 20). Along these same lines, the opening 60, 62 are preferably symmetric relative to the mid-line M. While the openings 60, 62 project, in one embodiment, through an entire thickness of the central body 22, in alternative embodiments, the openings 60, 62 are defined as recesses from an interior surface (shown in FIG. 1) of the central body 22 (and thus do not extend through an entirety of the central body 22 thickness). Further, the first and second openings 60, 62 can assume a variety of other shapes, and more or less than two of the openings 60, 62 can be formed. For example, in one alternative embodiment, a single, enlarged opening is provided in the top portion 40. In other embodiments, one or both of the openings 60, 62 can be eliminated. Where provided, however, the openings 60, 62 are preferably spaced from the sagittal mid-line such that when a rear of a patient's head is wrapped within the top portion 40, sufficient material surface area is provided to support the patient's head relative to a surface on which the patient is lying.

To assist in wrapping the central body 22 about a rear of the patient's head, in one embodiment the top portion 40 further forms a plurality of slits 64 (referenced generally). The slits 64 are generally horizontally disposed (i.e., generally perpendicular to the mid-line M), and are centrally positioned between the opening 60, 62. Any number of the slits 64 can be provided (i.e., more or less than the three slits 64 illustrated in FIG. 1), and can be spatially oriented in directions different from that shown. To this end, in one alternative embodiment, a multiplicity of closely spaced slits 64 are formed, extending in different spatial directions and combining to define a webbing that collectively replaces the openings 60, 62. However, with the one embodiment shown, the slits 64 include first-fourth slits 64a-64d. The first slit 64a constitutes an inferior-most slit and, as made clear below, will be positioned at or immediately adjacent the patient's occipital bone during use. With this in mind, in one embodiment, the first slit 64a has a wavy or scalloped-like shape so as to distribute any pressure points along an enlarged surface area. Further, the third and fourth slits 64c, 64d are generally convex in shape relative to the coronal mid-line CM (and thus relative to the occipital bone of the patient's head during use) to minimize or eliminate possible pressure points, as well as to promote cupping or three-dimensional curving of the top portion 40 about a rear of the patient's head as previously described. Alternatively, the slits 64 can assume a variety of other forms and, in alternative embodiments, can be eliminated.

The bottom portion 42 extends inferiorly from the top portion 40, increasing in width to the bottom end 46 as shown. As a point of reference, while the top and bottom portions 40, 42 are described as being separate components, in one embodiment, the central body 22 is formed as a continuous, homogenous structure such that a line of demarcation between the top and bottom portions 40, 42 does not physically exist. Regardless, in one embodiment, the bottom portion 42 is sized and shaped to define a width large enough to cover both ears of an infant patient's head (with the central body 22 centered on a read of the patient's head), and lies or bears against a nape of the patient's neck during use. With this in mind, in one embodiment a middle perimeter region 66 of the bottom end 46 is wavy or scalloped-shaped to minimize possible pressure points on the patient's head, and in the flat state, is generally concave. Opposing outer perimeter regions 68a, 68b of the bottom end 46 are generally linear (in the flat state), establishing a desired orientation of the lower straps 28, 30 as described below. In one embodiment, the outer perimeter regions 68a, 68b define an angle relative to the sagittal mid-line SM in the range of 50-85 degrees. In the wrapped state, the angle of outer perimeter region 68a, 68b extension, and thus the angle of the lower straps 28, 30, dictates a location of the lower straps 28, 30 relative to the patient's upper lip, and thus is selected to correspond with an anticipated size of the patient's head. For example, for very small infants (e.g., head circumference in the range of 17-26 cm), the angle of outer perimeter region 68a, 68b extension relative to the sagittal mid-line SM can be on the order of 73-83 degrees; whereas for larger infant patients (e.g., head circumference in the range of 26-42 cm), the angle of outer perimeter region 68a, 68b extension relative to the sagittal mid-line SM can be on the order of 55-65 degrees. Alternatively, other dimensions are acceptable. Even further, the bottom portion 42 can assume a wide variety of other shapes and sizes apart from those shown in alternative embodiments.

To enhance long-term patient comfort, in one embodiment, the headgear 20 further includes an occipital pad 80 disposed on the interior surface 21 within the bottom portion 42. As described below, the primary pad 80 directly contacts the patient's head immediately inferior the occipital bone. In one embodiment, the occipital pad 80 is comprised of a soft, cushioning material (e.g., foam), and is sized to provide an enhanced surface area, preferably encompassing a majority of an available lateral space between the first slit 64a and the bottom end 46. For example, in one embodiment, the occipital pad 80 has a length in the range of 2.5-3.0 inch (preferably approximately 2.75 inches) and a width in the range of 0.25-0.75 inch (preferably approximately 0.5 inch), and is centered relative to the sagittal mid-line SM, although other dimensions and/or locations are also acceptable. Notably, the occipital pad 80 is not a required component and thus, in alternative embodiments, can be eliminated.

The forehead straps 24, 26 are, in one embodiment, identical, extending from a corresponding one of the sides 48 or 50 of the central body 22 at a point laterally (inferiorly) spaced from the top end 44. Each of the forehead straps 24, 26 generally defines a trailing segment 90 and a leading segment 92. The trailing segment 90 is attached to, and extends directly from, the central body 22. The leading segment 92 extends from the trailing segment 90, and terminates at a leading end 94. As shown in FIG. 1, in the flat state, the forehead straps 24, 26 are symmetrically arranged relative to the sagittal mid-line SM, and extend in a non-colinear fashion relative to one another. To this end, and in one embodiment, in the flat state, the trailing segment 90 extends in a first spatial orientation or direction D1 from the central body, whereas the leading segment 92 extends in a second spatial orientation or direction D2 from the trailing segment 90. The first orientation D1 differs from the second orientation D2, such that forehead straps 24, 26 each have a non-linear configuration in the flat state. More particularly, in the flat state, the trailing segment 90 projects superiorly from the central body 22 (i.e., toward the top end 44), whereas the leading segment 92 projects inferiorly from the trailing segment (i.e., toward the bottom end 46). Thus, the orientation direction D1 of the trailing segment 90 intersects with the bottom portion 42 of the central body 22 such that during use, a primary "line" of attachment is established from the forehead straps 24, 26 to the bottom portion 42 as described below. Further, the differently oriented leading segment 92 readily wrap about or to the patient's forehead. In one embodiment, the forehead straps 24, 26 have a curved perimeter shape. Alternatively, the forehead straps 24, 26 can assume a variety of other shapes and need not be identical.

As made clear below, the forehead straps 24, 26 are, during use, wrapped toward or about the patient's forehead during use. Thus, an overall length collectively defined by the forehead straps 24, 26 (i.e., transverse distance between the leading ends 94) can assume a number of different dimension. In fact, because the forehead straps 24, 26 will overlap one another to a certain extent during use, the forehead strap 24, 26 designs can accommodate a fairly wide range of patient head sizes. In one embodiment, however, the forehead straps 24, 26 are sized for use with a select range of infant patient head sizes. For example, in one embodiment, the forehead straps 24, 26 define a collective length (i.e., distance between the leading ends 94) in the range of 10.4-11.4 inches for use with an infant patient having a head circumference in range of 17-21 cm; a collective length in the range of 11.3-12.2 inches for use with an infant patient having a head circumference in the range of 21-26 cm; a collective length in the range of 13.7-14.7 inches for use with an infant patient having a head circumference in the range of 26-32 cm; a collective length in the range of 15.3-16.3 inches for use with an infant patient having a head circumference in the range of 32-37 cm; and a collective length in the range of 16.0-17.0 inches for use with an infant patient having a head circumference in the range of 37-42 cm. Alternatively, however, the forehead straps 24, 26 can be sized to define a number of other collective lengths.

In one embodiment, the headgear 20 is adapted such that when applied to a patient, the first forehead strap 24 lies against the patient's forehead and the second forehead strap 26 overlies the first forehead strap 24. With this in mind, in one embodiment, the headgear 20 further includes a forehead pad 100 applied to the interior surface 21 along the first forehead strap 24, a first engagement strip 102 applied to the interior surface 21 along the second forehead strap 26, and a second engagement strip 104 applied to the exterior surface (hidden in FIG. 1) along the first forehead strap 24.

The forehead pad 100 is adapted to be comfortable when pressed against the patient's skin, and can thus assume a variety of forms (e.g., a foam pad). Further, the forehead pad 100 provides a tacky surface (as compared to a coefficient of friction associated with the material otherwise forming the interior surface 21 along at least the first forehead strap 24). This tacky surface does not readily slide along a patient's skin, a common problem found with prior headgear designs. As a result, a user will not be inclined to over tighten the headgear in an effort to prevent slipping of the headgear 20. Regardless, the forehead pad 100 is preferably applied to the first forehead strap 24 so as to be centered relative to a center of the leading end 94 thereof, and is off-set therefrom. Alternatively, the forehead pad 100 can be placed in a location differing from that shown, and in some embodiments is eliminated.

Similarly, the engagement strip 102 can assume a variety of forms, and is configured in accordance with a material comprising an exterior surface (hidden in FIG. 1) of headgear 20 and in particular the first forehead strap 24. More particular, and as described below, in one embodiment, the exterior surface comprises a loop-type material, at least along the first forehead strap 24. With this in mind, in one embodiment, the engagement strip 102 is a strip or tab of hook-type material such that when the second forehead strap 26 is wrapped over the first forehead strap 24 (i.e., the interior surface 21 of the second forehead strap 26 is above or on top of the exterior surface of the first forehead strap 24), the engagement strip 102 will releasably couple or engage the first forehead strap 24 (e.g., a Velcro®-type engagement).

To minimize possible patient discomfort caused by pressing of the second forehead strap 26 on to the patient and/or movement of the patient's head relative to the second forehead strap 26, in one embodiment, manufacture of the headgear 20 includes ultrasonically welding the engagement strip 102 to the second forehead strap 26 in a manner that ensures all side edges 104 (referenced generally) of the strip 102 are flat against the second forehead strap 26. To this end, it is known in the ultrasonic welding art to employ an ultrasonic horn or anvil that defines a plurality of line projections that otherwise effectuate a weld between to materials when subjected to ultrasonic energy (e.g., the line projections extend generally perpendicular to a length engagement strip 102 shown in FIG. 1). With this approach, it is difficult to consistently ensure that an individual line projection is over the opposing edges of the engagement strip 102 (in a manner that would otherwise cause the edges to be welded flat against the second forehead strap 26). This is especially true under manufacturing conditions where the headgear 20 is produced in mass, and a supply of engagement strips 102 has varying sizes and/or where the engagement strip 102 is hand applied to the second forehead strap 26 (thus entailing some inherently variability in an exact location of the engagement strip 102 relative to the second forehead strap 26). As such, in one embodiment, a method of manufacturing the headgear 20 in accordance with principles of the present invention includes use of an ultrasonic horn or anvil having line projections, the outer two of which are of an increased width, for ultrasonically welding the engagement strip 102 to the second forehead strap 26. With this approach, even where the engagement strip 102 has a size slightly varying from an expected size and/or the engagement strip 102 is located on the second forehead strap 26 in position slightly different from that expected, the outer two line projections will cover the opposing edges of the engagement strip 102 to ensure a complete, flat weld. Alternatively, the engagement strip 102 can assume a number of other forms (e.g., can be a loop-type material), and can be assembled to the second forehead strap 26 in a variety of different manners (e.g., adhesive). Even further, in other embodiments, the engagement strip 102 is eliminated.

In some embodiments, the second engagement strip 104 is also provided and is assembled to the first forehead strap 24 along the exterior surface thereof (and thus is hidden in the view of FIG. 1). The second engagement strip 104 is, in one embodiment, similar to the first engagement strip 102 described above, and thus can be a strip of hook-type material. The second engagement strip 104 is positioned between the forehead pad 100 and the leading end 94 of the first forehead strap 24. Alternatively, the second engagement strip 104 can be eliminated, such as where the first forehead strap 24 is of a smaller length.

The lower straps 28, 30 are, in one embodiment, identical and are symmetrically disposed relative to the sagittal midline SM. As described below, the lower straps 28, 30 do not provide a primary means of attaching the headgear 20 to a patient's head, and thus have a width that is less than a width of the forehead straps 24, 26. Regardless, the lower straps 28, 30 are spaced relative to the forehead straps 24, 26, respectively; for example, the first lower strap 28 is inferiorly spaced from the first forehead strap 24 (i.e., laterally spaced in a direction opposite the top end 44), whereas the second lower strap 30 is inferiorly spaced from the second forehead strap 26. Further, and as previously described, the lower straps 28, 30 extend contiguously from a corresponding one of the outer perimeter regions 68a, 68b of the central body 22.

In one embodiment, a transition zone 110a, 110b between corresponding pairs of the forehead and lower straps 24/28, 26/30 has a curved perimeter shape as illustrated in FIG. 1. This curved transition zone 110a, 110b serves as a relief area, ensuring that when the headgear 20 is applied to a patient's head in the wrapped state, the patient's eyes are not encumbered, as described below.

In one embodiment, the lower straps 28, 30 are directly connected or threaded to a corresponding component of the patient airway interface system (not shown), and folded back on to themselves. With this in mind, in one embodiment, the headgear 20 further includes first and second engagement tabs 112a, 112b secured to, and extend from, respective ones of the lower straps 28, 30. The engagement tabs 112a, 112b can assume a variety of forms, and are generally configured in accordance with a material comprising the exterior surface of the headgear 20 so as to facilitate releasable engagement between the engagement tab 112a or 112b and the exterior surface of the headgear 20. For example, in one embodiment where the exterior surface of the headgear 20 is comprised of a loop-type material, the engagement tabs 112a, 112b include a hook-type surface. With this embodiment, the engagement tabs 112a, 112b are arranged such that the hook-type surface is exterior exposed (and thus hidden in the view of FIG. 1). During use, then, as the lower straps 28, 30 are wrapped back on to themselves, the exposed hood-type surfaces of the engagement tabs 112a, 112b will readily engage the exterior surface of the headgear 20 (e.g., a Velcro™-type attachment). Alternatively, the engagement tabs 112a and/or 112b can assume a variety of other forms (e.g., a pressure sensitive adhesive-bearing structure), and in other embodiments are eliminated.

The vertical strap 32 extends vertically (in the flat state) from the top end 44 along the sagittal mid-line SM, terminating at a forward end 120. As described below, the vertical strap 32 serves to support or cushion the patient's head against various patient airway interface system components, and keeps the headgear 20 from sliding inferiorly (downwardly) along the patient's once applied. As such, the vertical strap can assume a number of different shapes and sizes. In one embodiment, however, the vertical strap 32 defines opposing edges 122a, 122b, at least a portion of which has a wavy or scalloped-shape to minimize possible pressure points when pressed against a patient's head. Alternatively, the vertical strap 32 can have a more linear shape, and in other embodiments, can be eliminated entirely.

In one embodiment, the vertical strap 32 is configured to be partially wrapped about the patient's head during use. With this in mind, it has been discovered that with infant patients (especially pre-mature infants or neonates), it may be possible to "over tighten" the vertical strap 32, potentially leading to patient discomfort and even trauma. To minimize this over tightening from accidentally occurring, in one embodiment the vertical strap 32 forms a plurality of horizontally extending slits 124 (referenced generally) adjacent the central body 22. The slits 124 serve as visual indicators of over tightening, whereby a user will readily perceive when the slits 124 are overtly separating. Under these circumstances, the user will recognize that the vertical strap 32 has been over tightened, thus prompting the user to re-position the vertical strap 32 and/or select a differently sized headgear 20. This visual indication can be provided in a wide variety of other manners differing from the slits 124 as shown. In other embodiments, the slits 124 (or any other visual indicating means) are eliminated.

As described below, in one embodiment application of the headgear 20 to a patient entails partially wrapping of the vertical strap 32 back on to itself. In one embodiment, then, the headgear 20 further includes an engagement structure 126 (referenced generally) on the exterior surface along the vertical strap 32 (as a point of reference, the engagement structure 126 is hidden in the view of FIG. 1). The engagement structure 126 is configured in accordance with a material comprising the exterior surface of the vertical strap 32, and in particular is selected to releasably engage the exterior surface. Thus, where the exterior surface is formed of a loop-type material, the engagement structure 126 can be a strip or tab of hook-type material (e.g., a Velcro®-type arrangement). Alternatively, the engagement structure 126 can assume a variety of other forms, and in alternative embodiments can be eliminated.

The headgear 20 (including each of the central body 20, the forehead straps 24, 26, the lower straps 28, 30, and the vertical strap 32) is preferably formed of a soft, cushioning-type fabric material, and in one embodiment has multiple layers. For example, in one embodiment, the headgear 20 is comprised of an interior foam layer (e.g., polyester foam) that forms or defines the interior surface 21 and an exterior fabric material (e.g., nylon fabric) that forms or defines the exterior surface (hidden in FIG. 1). As alluded to above, the exterior material, and thus the exterior surface, is preferably selected to provide a continuous surface for releasably engaging corresponding headgear components (e.g., the exterior surface forms a multiplicity of micro-hooks (or micro-loops)) at any number of different exterior locations. Alternatively, the headgear 20 can be formed of other materials, can be a single layer and/or the various components can be formed of differing materials.

In one embodiment, the central body 20 and the straps 24-32 are formed as an integral, homogenous, contiguous structure, for example by punch cutting the headgear 20 (in the flat state of FIG. 1) from a sheet of appropriate material(s). Alternatively, one or more of the central body 20, the forehead straps 24, 26, the lower straps 28, 30 and/or the vertical strap 32 can be separately formed and subsequently assembled to the other component(s), for example by ultrasonic welding.

In conjunction with the one exemplary technique for applying the headgear 20 to a patient's head described below, in one embodiment, manufacture of the headgear 20 further includes placement of indicia on one or more of the central body 22 and/or the strap(s) 24-32 to prompt a user as to the desired application. For example, in one embodiment, the headgear 20 further includes first, second, and third instructional indicia 130a, 130b, and 130c oriented to be read via the exterior surface. The first instructional indicia 130a is provided on the first forehead strap 24 and is generally indicative of a first step (e.g., forms a "1"); the second instructional indicia 130b is provided on the vertical strap 32 and is generally indicative of a second step (e.g., forms a "2"); and the third instructional indicia 130c is provided on the second forehead strap 26 and is generally indicative of a third step (e.g., forms a "3"). With this one approach, then, a user will readily understand that the proper application steps include first applying the first forehead strap 24, followed by application of the vertical strap 32, and then followed by application of the second forehead strap 26. The instructional indicia 130a-130c can assume a variety of forms apart from that shown, and in other embodiments can be eliminated. Similarly, in other embodiments, the headgear 20 can further include size designation indicia 132, for example visible on the exterior surface along the central body 22. The size designation indicia 132 can assume a variety of forms, and can generally indicate an overall size of the headgear 20 (e.g., small, medium, large, etc.) and/or a patient head circumference range most appropriate for the particular headgear 20. In other embodiment, the size designation indicia 132 are eliminated. Where provided, however, the instructional indicia 130a-130c and the size designation indicia 132 are applied to the corresponding headgear component's surface by any number of techniques, such as heat transfer, screen printing, pad printing, etc.

Figure 2A:
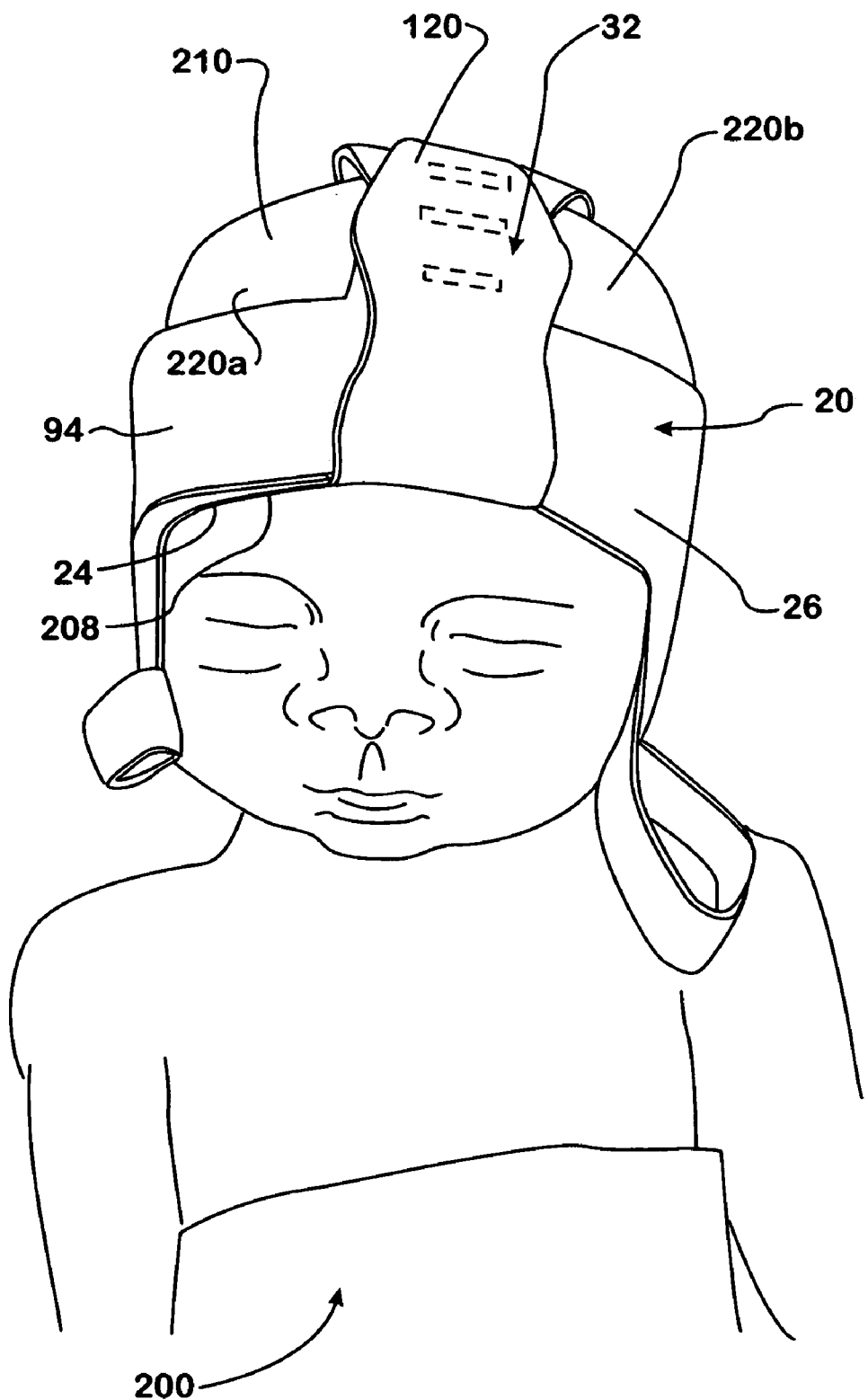
FIGS. 2A-2C illustrate application of the headgear to an infant patient.
Figure 2B:
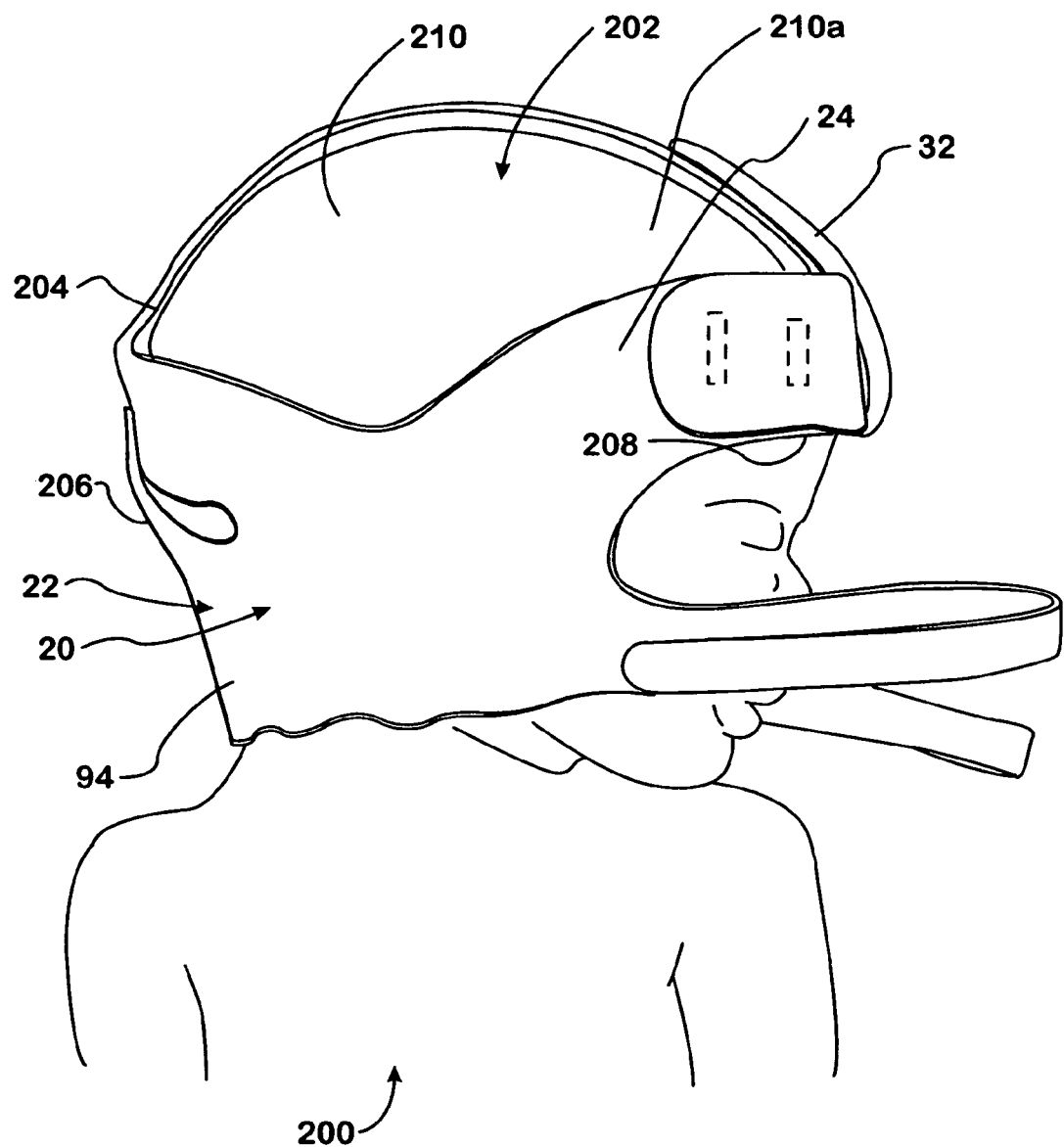
Figure 2C:
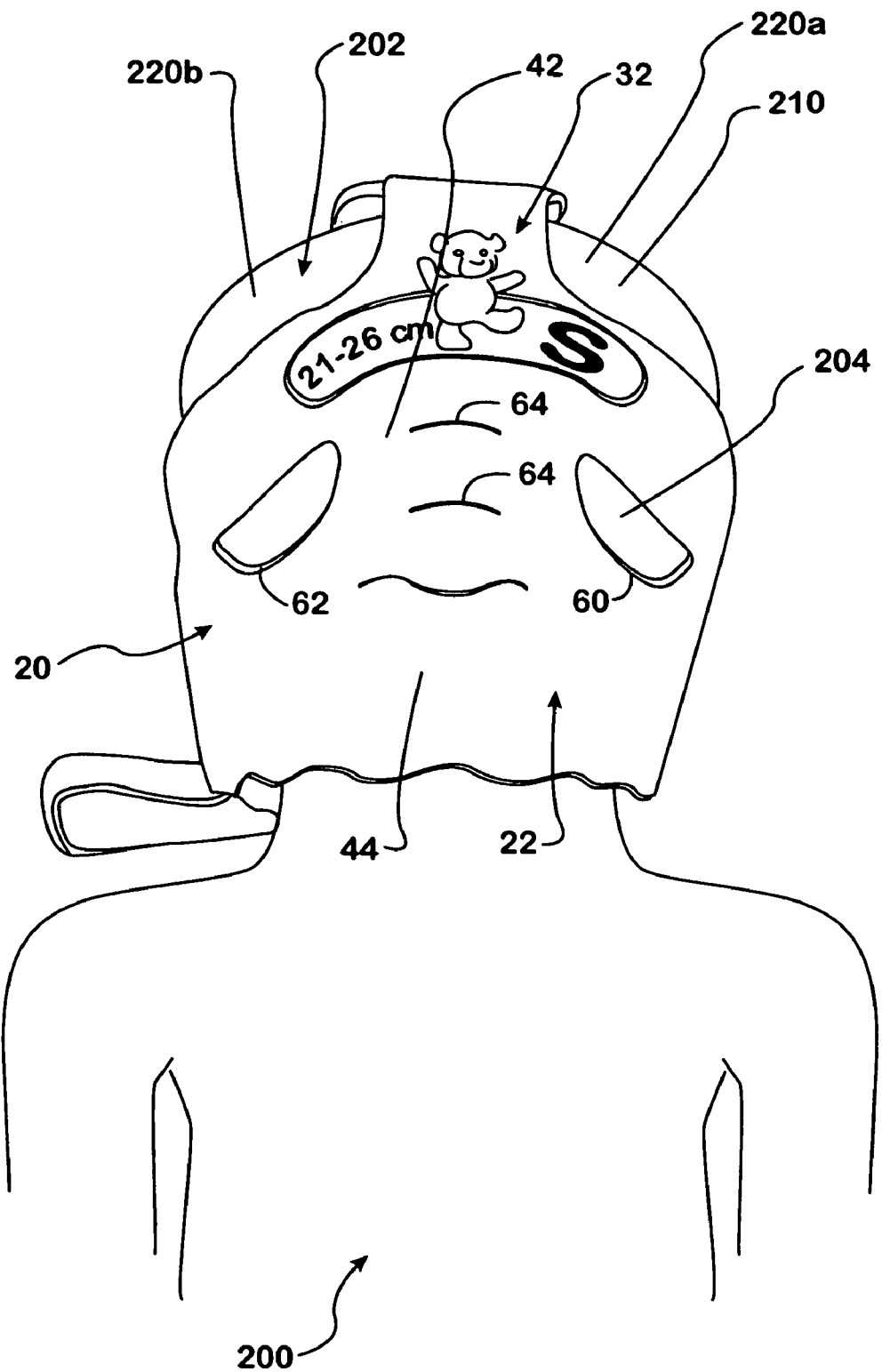

Application of the headgear 20 to an infant patient 200 in accordance with principles of the present invention is best described with continued reference to FIG. 1 as well as FIGS. 2A-2C. In one embodiment, a circumference of a head 202 (about the crown) is first determined, and an appropriately sized headgear selected. By way of reference, it has been found that the varying sizes commonly associated with infant heads (e.g., in the range of 17-42 cm) can be accommodated with only five differently sized version of the headgear 20 described above (whereby there primary difference in headgear 20 size in terms of the collective length defined by the forehead straps 24, 26 and the angle at which the lower straps 28, 30 extend from the central body 22). This represents a marked improvement over current bonnet-type infant headgear configurations whereby a highly large number of differently-sized bonnets must be inventoried. Regardless, with the desired size in mind, the headgear 20 is initially laid in the flat state of FIG. 1 (such as on a table), with the interior surface 21 facing outwardly (i.e., the orientation of FIG. 1). The infant's head 202 is then laid on to the headgear 20. In particular, a rear 204 (FIG. 2B) of the infant's head 202 is placed on to the central body 22, with the occipital bone/region 206 (reference generally in FIGS. 2B and 2C) being positioned at or slightly above the bottom portion 42 (FIG. 1). The infant's head 202 is preferably centered relative to the headgear 20 (i.e., relative to sagittal mid-line SM); the vertical strap 32 assists in achieving this desired positioning whereby the user can visually estimate whether the vertical strap 32 is centrally positioned relative to the infant's head 202 (i.e., in the flat state of FIG. 1, the vertical strap 32 is uncovered by the infant's head 202, providing a straightforward visual confirmation of an approximate centered position of the infant's head 202 relative to the central body 22).

With the infant's head 202 properly positioned on the central body 22, the first forehead strap 24 is wrapped over a forehead 208 of the infant 200 as best shown in FIG. 2A. In one embodiment, the first forehead strap 24 includes the first instructional indicia 130a (FIG. 1) that indicates to the user that the first forehead strap 24 should be applied first. Regardless, the first forehead strap 24 is placed across the forehead 208, with the forehead pad 100 (FIG. 1) abutting against the patient's forehead 208 at approximately a sagittal center of the patient.

The vertical strap 32 is then wrapped from the rear portion 204 toward the forehead 208, and placed on top of the previously-positioned first forehead strap 24. This relationship is best shown in FIGS. 2A and 2B. In one embodiment, the second instructional indicia 130b (FIG. 1) provides a visual clue to the user that the vertical strap 32 should be positioned following placement of the first forehead strap 24. Regardless, the vertical strap 32 is preferably centered relative to the forehead 208. Further, in one embodiment where the vertical strap includes the slits 124 (FIG. 1), the slits 124 provide a visual indication of vertical strap 32 over tightening in that if the vertical strap 32 is over tightened about the infant's head 200, the slits 124 will individually separate. If this situation is perceived by the user, the user will then reduce an applied tension to the vertical strap 32.

The second forehead strap 26 is then wrapped toward the patient's forehead 208, and is placed over the first forehead strap 24 and the vertical strap 32. The third instructional indicia 130c (FIG. 1) provides a visual indication that the second forehead strap 26 is the third strap to be applied to the patient 200 in succession. The second forehead strap 26 is generally aligned with a length of the previously-positioned first forehead strap 24. Once properly positioned, the leading end 94 of the second forehead strap 26 will extend beyond the vertical strap 32 (best shown in FIG. 2A) such that the engagement strip 102 (FIG. 1) contacts and engages the exterior surface 21 (referenced generally) of the first forehead strap 24.

When the straps 24, 26, 32 are properly positioned, the second forehead strap 26 should lie directly over the first forehead strap 24 and a bottom edge of both of the forehead straps 24, 26 should be approximately aligned with the patient's brow. The vertical strap 32 is then folded back on to itself, with the forward end 120 directed toward a crown 210 of the patient's head 200, as best shown in FIGS. 2A and 2B. With this arrangement, the engagement structure 126 (FIG. 1) otherwise carried by the vertical strap 32 readily contacts and engages the exterior surface 21 along a remainder of the vertical strap 32, thus securing the forward end 120. Once again, the slits 124 provide a visual indication of possible over tightening of the vertical strap 32.

With the straps 24, 26, and 32 applied as described above, the headgear 20 is now affixed to the patient's head 202. As shown in FIGS. 2B and 2C, the bottom portion 42 of the central body 22 resides immediately inferior the occipital bone or along a nape of the patient's neck (hidden in FIGS. 2B and 2C, but referenced generally at 212). Further, the central body 22 extends about and covers the patient's ears (not shown, but evident from the view of FIG. 2B). In one embodiment, however, the headgear 20 does not cover a majority of the patient's head 202, especially in the region of the crown 210. For example, in one embodiment, the applied headgear 20 (i.e., in the wrapped state) provides at two enlarged regions 220a, 220b at which the head/cranium 202 remains exposed, and thus readily available to receive auxiliary treatments (e.g., IV's). Further, the applied headgear 20 in the wrapped state establishes a line of engagement about the patient's head 202 that extends from and between the forehead 208 and the nape of the neck 212. In other words, unlike conventional headgear designs, the headgear 20 in accordance with principles of the present invention does not establish a line of engagement about or along the crown 210 as to do so might cause overt pressure points and/or deformation of the skull. In addition, and as best shown in FIG. 2C, the top portion 42 of the central body 22 assumes a three-dimensional state, wrapping or cupping about a contour of the rear 204 of the patient's head 202. That is to say, the central body 22 achieves a three-dimension fit about the rear 204 of the patient's head 202, thus providing complete support when the patient 200 is positioned with the head 202 lying on a surface. In this regard, the various features associated with one embodiment of the central body 22 (e.g., the openings 60, 62 and the slits 64) promote this desired, cupped fit and prevent formation of buckled material. Finally, the vertical strap 32 prevents the headgear 20 from sliding inferiorly or downwardly relative to the patient's head 202.

Figure 3:
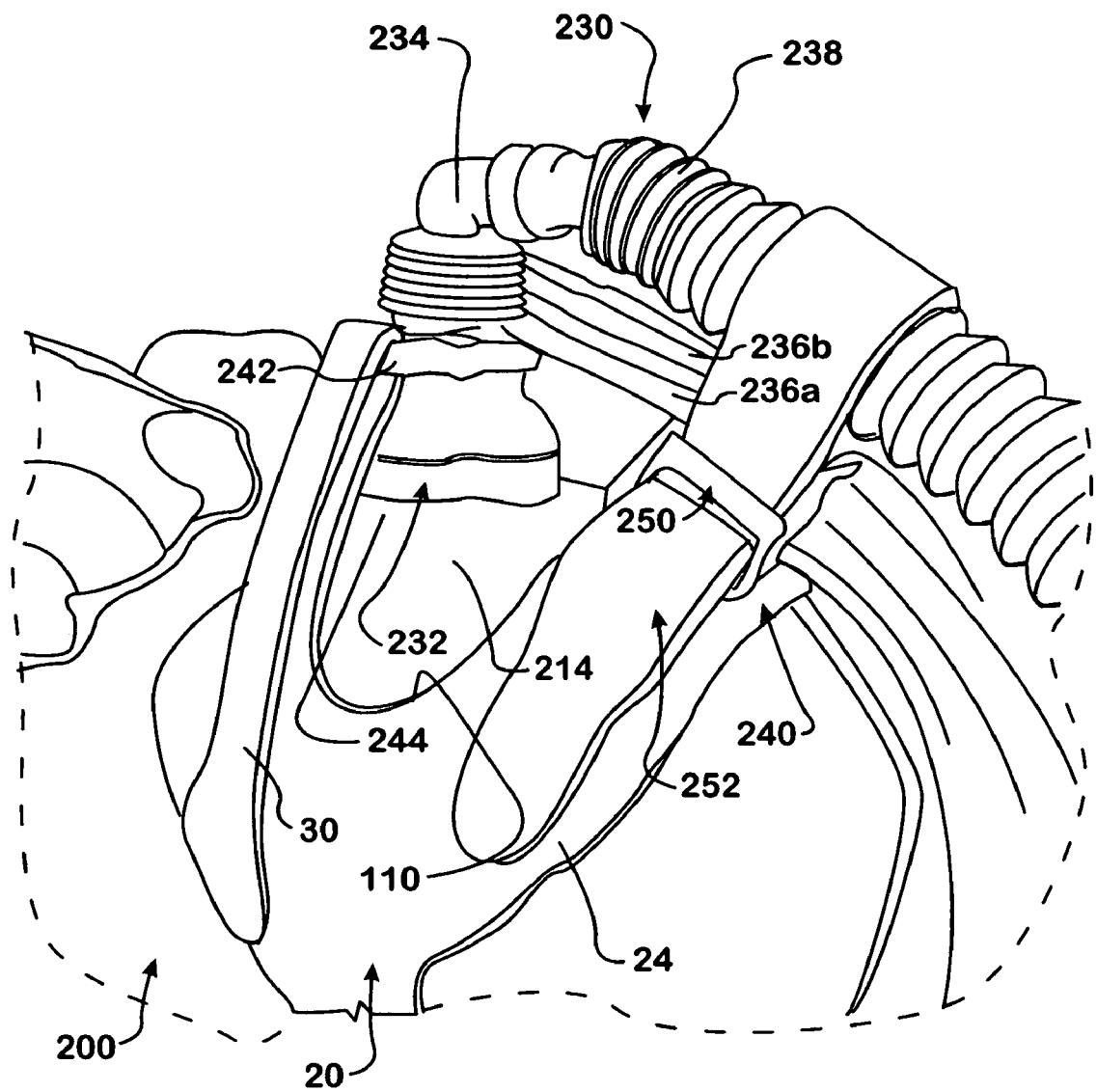
FIG. 3 illustrates the headgear of FIG. 1 in combination with one embodiment patient airway interface device in accordance with principles of the present invention.

Following application of the forehead straps 24, 26 and the vertical strap 32, the lower straps 28, 30 can then be deployed to connect an patient airway interface device to the headgear 20/patient 200. One embodiment of portions of a patient airway interface device 230 with which the headgear 20 is useful are illustrated in FIG. 3. In general terms, the patient airway interface device 230 is provided as part of an airway interface system, such as an nCPAP system. With this in mind, the interface device 230 generally includes an interface piece 232, a CPAP generator 234, inlet tubes 236a, 236b, an exhaust tube 238, and a support block assembly 240. It will be understood that the headgear 20 can be used with a wide variety of other airway interface devices that may or may not include one or more of the components 232-240; typically, however, at least the interface piece 232 will be provided, and is configured to establish a fluid connection with the patient's nasal airways (i.e., nares), and is in the form of a mask (as shown in FIG. 3), nasal prongs, etc.

With the above general description in mind, in one embodiment, the generator 234 includes connection bodies 242, one of which is referenced generally in FIG. 3. The connection bodies 242 can assume a variety of forms, and are configured to receive a respective one of the lower straps 28, 30 (e.g., such as by threading the lower straps 28, 30 through the corresponding connection body 242); in other embodiments, the interface piece 232 forms or provides the connection bodies 242. Regardless, and with additional reference to FIGS. 2A and 2B, the lower straps 28, 30 are wrapped toward an upper lip 244 (referenced generally) of the patient, and connected to a respective one of the connection bodies 242, as shown in FIG. 3. Once secured to the connection body 242, the lower strap 28 or 30 is then threaded back on to itself and secured, such as via the corresponding engagement strip 112 (FIG. 1) contacting the exterior surface 21 thereof. Notably, and as best shown in FIGS. 2B and 3, the transition zone 110 established between the corresponding pairs of forehead straps/lower straps 24/28, 26/30 fully accommodates the patient's eyes 214. This is of great benefit for infant patients whom might otherwise be highly sensitive to any contact with their eyes 214 or the immediately surrounding skin.

In embodiments where the patient airway interface device 230 includes components in addition to the interface piece 232/generator 234 that must otherwise be supported along the patient's head 202, the above steps can be modified slightly be first securing the support block assembly 240 to the headgear 20. As a point of reference, with the one embodiment of FIG. 3, the interface device 230 is provided in an assembled format, whereby the tubes 236a-238 are secured to the generator 234 and the support block assembly 240. To this end, the support block assembly 240 can include a support block 250 and a band 252 movably connected thereto. The tubes 236a-238 are pre-assembled to the support block 250, with the band 252 maintaining one or more of the tubes 236a-238 relative to the support block 250. With this in mind, assembly of the interface device 230 includes first fluidly connecting the interface piece 232 with the patient's nasal airways. The support block 250/tubes 236a-238 are then aligned mid-line with the patient's head 202. The support block 250 is then placed on to the second forehead strap 26, followed by securing of the band 252 on to the second forehead strap 26 (e.g., using Velcro®-type hook material/strip on an interior face of the band 252 to releasably engage the exterior surface 21 along the second forehead strap 26). Once positioned and secured, the lower straps 28, 30 can then be connected to the interface piece 232/generator 234 as previously described. Once assembly is complete, the tubes 236a-238 extend superiorly along the patient's head 202, with the vertical strap 32 providing a cushion between the tubes 236a-238 and the patient's head 202.

The headgear and related infant nasal airway interface system of the present invention provides a marked improvement over previous designs. The headgear effectively translates an easy-to-manufacture two-dimensional design or format into a three-dimensional device when wrapped about a patient's head. By establishing a line of attachment extending from the patient's forehead to the nape of the neck (e.g., immediately inferior the occipital bone), a more secure fit or attachment to the patient's head is achieved. Further, the headgear incorporates, in certain embodiments, other features, such as holes, scalloped-shaped edge(s), pads, etc., that are uniquely configured to minimize possible pressure points as well as allow for expected movements of the patient's head.

Although the present invention has been described with reference to preferred embodiments, workers skilled in the art will recognize that changes can be made in form and detail without departing from the spirit and scope of the present invention. For example, in alternative embodiments, an additional lateral strap can be provided that extends, when applied to the patient's head, from ear-to-ear, beneath the patient's chin. In other embodiments, one or more of the described straps can be provided with a recoil device that effectively generates a desired tension across the corresponding strap. Further, while the headgear has been described as preferably being applied to an infant patient, in other embodiments, the headgear can be sized for use with an adult or child.

What is claimed is:

1. A headgear for securing a patient airway interface device to a patient's head, such as an infant patient's head, the headgear being transitionable from a flat state to a wrapped state when applied to the patient's head, the headgear comprising:
   a central body defining, in the flat state, a top portion terminating in a top end and a bottom portion terminating in a bottom end, the central body adapted to be positionable at a rear of the patient's head whereby the bottom portion is adjacent an occipital bone of the patient's;
   first and second forehead straps extending from opposite sides, respectively, of the central body, wherein in the flat state, each strap includes a trailing segment extending from the central body and a leading segment extending from the trailing segment, the trailing segment extending in a first spatial direction and the leading segment extending in a second spatial direction, the second spatial direction differing from the first spatial direction; and
   first and second lower straps extending from opposite sides, respectively, of the central body, each lower strap being laterally spaced from a corresponding one of the forehead straps in a direction opposite the top end,
   wherein in the flat state, the leading segment of the first and second forehead straps extends in the second spatial direction toward the first and second lower straps.

2. The headgear of claim 1, wherein the headgear is adapted and sized such that when applied to a patient's head, the bottom portion rests against a nape of a neck of the patient's head and the forehead straps extend from opposite sides of the patient's head and intersect and partially overlap one another along a forehead of the patient to establish a line of attachment from the patient's forehead to an occipital region of the patient's head.

3. The headgear of claim 1, wherein the central body is sized and adapted such that the top portion conforms to a contour of a rear portion of a patient's head in the wrapped state.

4. The headgear of claim 1, wherein each of the forehead straps is configured such that in the flat state, the trailing segment projects from the central body in a direction generally away from the bottom end and the leading segment extends from the trailing segment in a direction generally toward the bottom end.

5. The headgear of claim 1, wherein each of the forehead straps defines opposing perimeter side edges, and further wherein in the flat state, at least one of the perimeter side edges defines a curvature along the leading segment.

6. The headgear of claim 1, wherein the central body is adapted and sized such that in the wrapped state and when the bottom portion is positionable adjacent an occipital bone of the patient's head, the top portion extends along a rear of the infant's head and the top end does not project over a crown of the patient's head.

7. The headgear of claim 1, wherein the top portion defines side edges extending from the top end to each of the forehead straps, and further wherein the side edges are curved.

8. The headgear of claim 1, wherein the central body forms first and second openings in the top portion.

9. The headgear of claim 8, wherein the first and second opening are symmetrically arranged relative to a mid-line of the central body.

10. The headgear of claim 8, wherein the first and second openings are kidney-shaped.

11. The headgear of claim 1, wherein the central body forms a plurality of slits.

12. The headgear of claim 11, where the slits extend in a direction generally perpendicular to a mid-line of the central body.

13. The headgear of claim 1, wherein the bottom end defines a bottom edge having a undulating, scalloped shape in the flat state.

14. The headgear of claim 1, further comprising a vertical strap extending from the top end of the central body.

15. The headgear of claim 14, wherein at least a portion of a perimeter of the vertical strap has a wavy, scalloped shape in the flat state.

16. The headgear of claim 14, wherein the vertical strap includes a plurality of slits formed in the vertical strap adjacent the central body.

17. The headgear of claim 14, wherein the central body, the forehead straps, the lower straps, and the vertical strap are integrally formed from a single material as a homogenous, contiguous body.

18. The headgear of claim 14, further comprising instructional indicia disposed along each of the forehead straps and the vertical strap, the instructional indicia providing an indication of an order in which the forehead straps and the vertical strap are applied to a patient.

19. The headgear of claim 1, wherein the headgear defines an interior surface and an exterior surface, the exterior surface formed of a loop-type material, the headgear further comprising:
   a strip of hook-type material applied to the interior surface along the second forehead strap.

20. A headgear for securing a patient airway interface device to a patient's head, such as an infant patient's head, the headgear transitionable from a flat state to a wrapped state when applied to the patient's head, the headgear comprising:
   a central body defining a top portion terminating at a top end and a bottom portion terminating at a bottom end, wherein the central body is sized and adapted to cover both ears of the patient's head and be positionable at a rear of the patient's head such that in the wrapped state, the bottom portion is adjacent an occipital bone of the patient's head and the top portion does not extend around to a front of the patient's head;
   first and second forehead straps extending from opposite sides, respectively, of the top end of the central body in the flat state, wherein the forehead straps are sized and adapted to be positionable across a forehead of the patient's head with the central body positioned at the rear of the patient's head in the wrapped state;
   wherein the forehead straps and the bottom portion combine to define, when in the wrapped state and applied to the infant's head, a line of attachment from the patient's forehead to a nape of a neck of the patient's head; and
   first and second lower straps extending from opposite sides of the central body, respectively, the lower straps being laterally spaced from a respective one of the forehead straps, and being sized and adapted to be positionable adjacent an upper lip of the patient's head;
   wherein the headgear is adapted such that when applied to the patient's head in the wrapped state, a portion of the patient's cranium is exposed.

21. The headgear of claim 20, wherein the central body is sized and adapted such that in the wrapped state, the top portion wraps about a rear of the patient's head, conforming to a contour thereof.

22. The headgear of claim 20, further comprising:
a vertical strap extending from the top end of the central body, the vertical strap being sized and adapted to be positionable to extend from a rear of the infant's head in a sagittal direction across the infant's head and intersect with the forehead straps.

23. A combination patient interface device and headgear for use as part of a patient airway interface system, such as an infant nCPAP system, the combination comprising:
a patient interface device comprising an interface piece for establishing a fluid connection with nasal airways of a patient; and
a headgear transitionable from a flat state to a wrapped state, the headgear defining an interior surface and opposing exterior surface in the flat state and comprising:
a central body defining, in the flat state, a top portion terminating at a top end and a bottom portion terminating at a bottom end, the central body being adapted to be positionable adjacent an occipital bone of a patient's head,
first and second forehead straps extending from opposite sides, respectively, of the central body, wherein in the flat state, each of the forehead straps includes a trailing segment extending from the central body in a first spatial direction and a leading segment extending from the trailing segment in a second spatial direction differing from the first, and further wherein a first engagement strip is disposed on the interior surface of the leading segment of the first forehead strap and a second engagement strip is disposed on the exterior surface of the leading segment of the second forehead strap,
first and second lower straps extending from opposite sides, respectively, of the central body, each of the lower straps being laterally spaced from a corresponding one of the forehead straps in a direction opposite the top end;
wherein the combination is configured such that in the wrapped state of the headgear, with the forehead straps extend from opposite sides of the patient's head to intersect and partially overlap one another along a forehead of the patient including the first engagement strip contacting the second forehead strap and the second engagement strip contacting the first forehead strap, the forehead straps and the central body securing the headgear to a patient's head, and the lower straps securing the patient interface piece to the headgear;
wherein in the flat state, the leading segment of the first and second forehead straps extends in the second spatial direction toward the first and second lower straps.

24. The combination of claim 23, wherein patient interface device further includes a CPAP generator and the interface piece includes a mask.

25. The combination of claim 24, wherein the patient interface device further includes a plurality tubes extending from the generator and a support block assembly spaced from the generator and maintaining the tubes, and further wherein the headgear is configured to receive the support block assembly in the wrapped state to support the support block assembly relative to a patient's forehead.

26. The combination of claim 25, wherein the headgear further includes a vertical strap extending from the top end of the central body, the headgear being configured such that upon assembly of the combination to a patient's head, the vertical strap supports at least one of the tubes.

27. The headgear of claim 1, wherein in the flat state, the leading segment of each of the forehead straps extends directly and continuously from the corresponding trailing segment.

28. The headgear of claim 1, wherein in the flat state, the leading segment of each of the forehead straps extends from the corresponding trailing segment in a direction opposite the central body.

* * * * *

UNITED STATES PATENT AND TRADEMARK OFFICE
CERTIFICATE OF CORRECTION

PATENT NO. : 7,878,200 B2
APPLICATION NO. : 11/354285
DATED : February 1, 2011
INVENTOR(S) : Chris Zollinger et al.

Page 1 of 1

It is certified that error appears in the above-identified patent and that said Letters Patent is hereby corrected as shown below:

Column 4, line 50, delete "sagitally" and insert in place thereof --sagittally--.

Column 7, line 28, delete "non-colinear" and insert in place thereof --non-collinear--.

Column 11, line 61, delete "there" and insert in place thereof --their--.

Signed and Sealed this
Twenty-sixth Day of April, 2011

David J. Kappos
*Director of the United States Patent and Trademark Office*